United States Patent [19]

Fieler et al.

[11] Patent Number: 4,728,457

[45] Date of Patent: Mar. 1, 1988

[54] PROCESS FOR MAKING A SILICONE-CONTAINING SHAMPOO

[75] Inventors: George M. Fieler; Larry V. Stacy, both of Cincinnati, Ohio

[73] Assignee: The Proctor & Gamble Company, Cincinnati, Ohio

[21] Appl. No.: 900,033

[22] Filed: Aug. 25, 1986

[51] Int. Cl.$^4$ ................................................. C11D 9/36
[52] U.S. Cl. .......................... 252/174.15; 252/174.16; 252/174.17; 252/174.21; 252/174.25; 252/544; 252/550; 252/555; 252/DIG. 13; 252/DIG. 17; 252/528; 252/547; 424/70
[58] Field of Search ................. 252/DIG. 13, 174.21, 252/550, 555, 544, 174.15, 174.17, 174.25, 174.16, DIG. 17, 528, 547; 424/70

[56] References Cited

U.S. PATENT DOCUMENTS

| | | | |
|---|---|---|---|
| 3,957,970 | 5/1976 | Korkis | 424/70 |
| 4,244,948 | 1/1981 | Boghosian et al. | 514/859 |
| 4,364,837 | 12/1982 | Pader | 252/DIG. 13 |
| 4,412,943 | 11/1983 | Hirota et al. | 252/DIG. 13 |
| 4,479,893 | 10/1983 | Hirota et al. | 252/DIG. 13 |

FOREIGN PATENT DOCUMENTS

| | | |
|---|---|---|
| 849433 | 9/1960 | United Kingdom . |
| 2170216 | 7/1986 | United Kingdom . |

*Primary Examiner*—Paul Lieberman
*Assistant Examiner*—Hoa Van Le
*Attorney, Agent, or Firm*—David K. Dabbiere; Douglas C. Mohl; Jack D. Schaeffer

[57] ABSTRACT

An improved process for making silicone containing shampoo wherein heated premixes are added to a main mix at ambient temperature.

5 Claims, No Drawings

PROCESS FOR MAKING A SILICONE-CONTAINING SHAMPOO

TECHNICAL FIELD

This invention relates to an improved process for manufacturing silicone-containing shampoos.

BACKGROUND

The use of silicones in shampoos is well known in the art. Publications include U.S. Pat. No. 2,826,551, Geen, issued Mar. 11, 1958; U.S. Pat. No. 3,964,500, Drakoff, issued June 22, 1976; U.S. Pat. No. 4,364,837, Pader, issued Dec. 21, 1982; British Pat. No. 849,433, Woolston, issued Sept. 28, 1960; U.S. Pat. No. 4,341,799, Good, issued July 27, 1982; and U.S. Pat. No. 4,465,619, Boskamp, issued Aug. 14, 1984.

While these patents disclose silicone-containing compositions, they do not provide answers to all of the problems associated with making a satisfactory product. One persistent problem has been that of developing effective processing steps for a product containing a dispersed, insoluble, nonvolatile silicone material.

The conventional means for making such silicone-containing shampoos has been to heat a mix of ingredients and stir them together. The silicone was either simply mixed in or, as in U.S. Pat. No. 3,964,500, Drakoff, issued June 22, 1976, the silicone was added subsequent to the other ingredients. This method of processing is energy intensive and may result in some undesirable breakdown of the product ingredients.

It has been surprisingly found that by using an improved process not only is energy saved but a more stable homogeneous product can be formed.

It is therefore an object of the invention to provide an improved process for making silicone-containing shampoos.

It is a further object of the invention to provide a cold process for making silicone-containing shampoos wherein only a portion of the ingredients are heated.

It is a further object of the invention to provide a process which uses two or more heated premixes injected sequentially into a main mix at ambient temperature.

It is a further object of the invention to provide a process for producing a stable, homogeneous pearlescent silicone-containing shampoo.

It is a further object of the invention to provide stable homogeneous silicone-containing shampoos produced by a cold process.

These and other objects of the invention will become clear from the description of the invention herein.

Where "ambient" or "ambient temperature" is used herein, a range of from about 60° F. to about 100° F. is indicated.

All percentages and ratios herein are by weight on a total composition basis unless otherwise noted.

SUMMARY OF THE INVENTION

Processes of the present invention comprise the steps of:
(a) preparing a first premix containing surfactant and a suspending agent;
(b) preparing a second premix containing the silicone:
(c) heating said premixes separately to from about 150° F. to about 170° F.;
(d) injecting said premixes into a main mix which is at ambient temperature;
(e) mixing; and
(f) cooling.

DETAILED DESCRIPTION OF THE INVENTION

The processes of the present invention provide stable silicone-containing shampoos. The various ingredients, essential and optional, are discussed in detail below, followed by the process steps.

ESSENTIAL INGREDIENTS

Surfactant

An essential component of the present compositions is a surfactant. The surfactant, which may be selected from any of a wide variety of synthetic anionic, amphoteric, zwitterionic and nonionic surfactants, is present at a level of from about 5% to about 60%, preferably from about 10% to about 30%, most preferably from about 10% to about 22%.

Synthetic anionic surfactants can be exemplified by the alkali metal salts of organic sulfuric reaction products having in their molecular structure an alkyl radical containing from 8–22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and other known in the art.

Zwitterionic surfactants can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

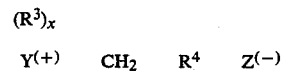

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxy-propane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxypentane-1-sulfate.

Other zwitterionics such as betaines are also useful in the present invention. Examples of betaines useful herein include the high alkyl betaines such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxy-ethyl) carboxy methyl betaine, stearyl bis-(2-hydroxy-propyl) carboxymethyl betaine, oleyl dimethyl gamma-carboxpropyl betaine, lauryl bis-(-2-hydroypropyl) alpha-carboxyethyl betaine, etc. The sulfobetaines may be represented by coco dimethyl sulfopropyl betaine, stearyl dimethyl sulfopropyl betaine, lauryl dimethyl sulfoethyl betaine, lauryl bis-(2-hydroxy-ethyl) sulfopropyl betaine and the like; amido betaines and amidosulfobetaines, wherein the RCONH(CH$_2$)$_3$ radical is attached to the nitrogen atom of the betaine are also useful in this invention. The amido betaines are preferred for use in some of the compositions of this invention. A particularly preferred composition utilizes an amido betaine, a quaternary compound, a silicone, a suspending agent and has a pH of from about 2 to about 4.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

$$R_1R_2R_3N \rightarrow O$$

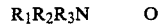

wherein R$_1$ contains an alkyl, alkenyl or monohydroxy alkyl radical of from about 8 to about 18 carbon atoms, from 0 to about 10 ethylene oxide moieties, and from 0 to 1 glyceryl moiety, and R$_2$ and R$_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyloctylamine oxide, dimethyl-decylamine oxide, dimethyltetradecylamine oxide, 3,6,9-trioxaheptadecyldiethylamine oxide, di(2-hydroxyethyl)-tetradecylamine oxide, 2-dodecoxyethyl-dimethylamine oxide, 3-dodecoxy-2-hydroxypropyl-di(3-hydroxypropyl)amine oxide, dimethylhexadecylamine oxide.

5. Long chain tertiary phosphine oxides corresponding to the following general formula:

$$RR'R''P \rightarrow O$$

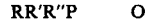

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxpropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)-phosphine oxide, dodecyldi(2-hydroxyethyl)phosphine oxide, tetradecylmethyl-2-hydroxydodecyldimethylphosphine oxide, oleyldimethylphosphine oxide, 2-hydroxdodecydodecyldimethylphosphine oxide. oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Many additional nonsoap surfactants are described in McCUTCHEON'S DETERGENTS AND EMULSIFIERS, 1979 ANNUAL, published by Allured Publishing Corporation, which is incorporated herein by reference.

The above-mentioned surfactants can be used alone or in combination in the shampoo compositions of the present invention. The anionic surfactants, particularly the alkyl sulfates, the ethoxylated alkyl sulfates and mixtures thereof are preferred for use herein as well as the amido betaines.

VISCOSITY MODIFIERS

Compositions herein comprise from about 0.1% to about 10% of a viscosity modifier. Preferred viscosity modifiers are hydrotropes such as aromatic sulfonates or ethyl alcohol. Preferred hydrotropes are ammonium xylene sulfonate, potassium toluene sulfonate and sodium cumene sulfonate. Ammonium xylene sulfonate is particularly preferred.

Other viscosity modifiers may also be used in compositions herein. Sodium chloride, sodium sulfate, isopropyl alcohol and polyvinyl alcohol are examples of other viscosity modifiers which may be present. Mixtures of viscosity modifiers are also suitable for use in compositions of the invention.

NON-VOLATILE SILICONE FLUID

Silicone fluids are suitable non-volatile silicone that may be used in the present compositions.

The non-volatile silicone fluid may be either a polyalkyl siloxane, a polyaryl siloxane, a polyalkylaryl siloxane or a polyether siloxane copolymer and is present at a level of from about 0.1% to about 10.00% preferably from about 0.5% to about 5.0%. Mixtures of these fluids may also be used and are preferred in certain executions. The dispersed silicone particles should also be insoluble in the shampoo matrix. This is the meaning of "insoluble" as used hereinbefore and hereinafter.

The essentially non-volatile polyalkyl siloxane fluids that may be used include, for example, polydimethyl siloxanes with viscosities ranging from about 5 to 600,000 centistokes at 25° C. These siloxanes are available, for example, from the General Electric Company as the Viscasil series and from Dow Corning as the Dow Corning 200 series. The viscosity can be measured by means of a glass capillary viscometer as set forth in Dow Corning Corporate Test Method CTM0004, July 20, 1970. Preferably the viscosity ranges from about 15,000 centistokes to about 100,000 centistokes.

The essentially non-volatile polyalkylaryl siloxane fluids that may be used include, for example, polymethylphenylsiloxanes having viscosities of about 15 to 30,000 centistokes at 25° C. These siloxanes are available, for example, from the General Electric Company as SF 1075 methyl phenyl fluid or from Dow Corning as 556 Cosmetic Grade Fluid.

The essentially non-volatile polyether siloxane copolymer that may be used is, for example, a polypropylene oxide modified dimethylpolysiloxane (e.g., Dow Corning DC-1248) although ethylene oxide or mixtures of ethylene oxide and propylene oxide may also be used.

References disclosing suitable silicone fluids include the previously mentioned U.S. Pat. No. 2,826,551, Geen, issued Mar. 11, 1958; U.S. Pat. No. 3,964,500, Drakoff, issued June 22, 1976; U.S. Pat. No. 4,364,837, Pader, issued Dec. 21, 1982; and British Pat. No. 849,433, Woolston, published Sept. 28, 1960. All of these patents are incorporated herein by reference. Also incorporated herein by reference is *Silicon Compounds* distributed by Petrarch Systems, Inc., 1984. This reference provides a very good listing of suitable silicone materials.

Another silicone material found especially useful in the present compositions to provide good dry combing is a silicone gum. Silicone gums described by Petrarch and others including U.S. Pat. No. 4,152,416, Spitzer et al., issued May 1, 1979 and Noll, Walter, *Chemistry and Technology of Silicones,* New York: Academic Press 1968. Also describing silicone gums are General Electric Silicone Rubber Product Data Sheets SE 30, SE 33, SE 54 and SE 76. All of these described references are incorporated herein by reference. "Silicone gum" materials denote high molecular weight polydiorganosiloxanes having a mass molecular weight of from about 200,000 to about 1,000,000. Specific examples include polydimethylsiloxane, (polydimethylsiloxane) (methylvinylsiloxane) copolymer, poly(dimethylsiloxane) (diphenyl) (methylvinylsiloxane) copolymer and mixtures thereof.

SUSPENDING AGENT

Suspending agents useful in the present compositions include any of several long chain acyl derivative materials or mixtures of such materials. Included are ethylene glycol esters of fatty acids having from about 16 to about 22 carbon atoms. Preferred are the ethylene glycol stearates, both mono and distearate, but particularly the distearate containing less than about 7% of the mono stearate. Other suspending agents found useful are alkanol amides of fatty acids, having from about 16 to about 22 carbon atoms, preferably about 16 to 18 carbon atoms. Preferred alkanol amides are stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide DEA distearate, stearamide MEA stearate).

Xanthan gum is another useful agent in the present compositions to suspend the silicone fluid. This biosynthetic gum material is commercially available and is a heteropolysaccharide with a molecular weight of greater than 1 million. It is believed to contain D-glucose, D-mannose and D-glucuronate in the molar ratio of 2.8:2.0:2.0. The polysaccharide is partially acetylated with 4.7% acetyl. This information and other is found in Whistler, Roy L. Editor *Industrial Gums—Polysaccharides and Their Derivatives* New York: Academic Press, 1973. Kelco, a Division of Merck & Co., Inc. offers xanthan gum as Keltrol$^R$. The gum is preferably used in combination with other suspending agents. When present the gum is used at a level of from about 0.3% to about 3%, preferably from about 0.4% to about 1.2% in the compositions of the present invention.

Still other suitable suspending agents are alkyl ($C_{16-22}$) dimethyl amine oxides such as stearyl dimethyl amine oxide. If the compositions contain an amine oxide or a long chain acyl derivative as a surfactant the suspending function could also be provided and additional suspending agent may not be needed if the level of those materials are at least the minimum level given below.

Preferred compositions employ one or more suspending agents comprising from about 0.5% to about 5.0%, preferably from about 0.5% to about 3.0% of the total composition. The suspending agents serve to assist in suspending the silicone material and may give pearlescence to the product. Mixtures of suspending agents are particularly suitable for use in the preferred compositions of this invention.

WATER

Water is the last essential component of the present invention and forms the remainder of the composition. It is generally present at a level of from about 20% to about 95%, preferably from about 60% to about 85%.

OPTIONAL COMPONENTS

The shampoos herein can contain a variety of nonessential optional components suitable for rendering such compositions more acceptable. Such conventional optional ingredients are well known to those skilled in the art, e.g., pearlescent aids such as ethylene glycol distearate (if not used as a suspending agent); preservatives such as benzyl alcohol, methyl paraben, propyl paraben and imidazolidinyl urea; cationic surfactants such as, tricetyl methyl ammonium chloride, cetyl trimethyl ammonium chloride, stearyldimethyl benzyl ammonium chloride, and di(partially hydrogenated tallow) dimethylammonium chloride; thickeners such as a diethanolamide of a long chain fatty acid (e.g., PEG 3 lauramide), cocomonoethanol amide, amine oxides, block polymers of ethylene oxide and propylene oxide such as Pluronic F88 offered by BASF Wyandotte, pH adjusting agents such as citric acid, sodium citrate, succinic acid, phosphoric acid, sodium hydroxide, sodium carbonate, etc.; perfumes; dyes; and, sequestering agents such as disodium ethylenediamine tetraacetate. Such agents generally are used individually at a level of from about 0.01% to about 10%, preferably from about 0.5% to about 5.0% by weight of the composition.

Another optional ingredient and one preferred for use in certain of the compositions of this invention, is a volatile silicone or a water insoluble hydrocarbon. These agents are disclosed in U.S. Pat. No. 4,472,375, R. E. Bolich, Jr., issued Sept. 18, 1984 incorporated herein by reference. These agents help disperse the higher molecular weight, non-volatile silicones in the product when the product is used. These agents are used at levels from about 0.1% to about 5%.

Another optional ingredient preferred herein is an alkyl ethoxylated phosphoric acid monoester (phosphate ester) or salt thereof. The phosphate esters useful in compositions of the invention provide static control. By helping to eliminate the static charge which builds up on the hair, the phosphate esters prevent "flyaway" hair.

When used, the phosphate esters are present at a level of from about 0.1% to about 5%, preferably from about 0.4% to about 2%.

Preferred phosphate esters are laureth-3-phosphate, laureth-4-phosphate, oleth-3-phosphate, laureth-5-phosphate, and tridecth-6-phosphate. Suitable salts of these esters include e.g., sodium, potassium, ammonium, lithium, monoethanolamine, diethanolamine, and triethanolamine. Further information on suitable alkyl phosphate monoesters may be found in U.S. Pat. No. 4,479,893, Hirota et al, issued Oct. 30, 1984.

The pH of the present compositions is not critical and may be in the range of from 4 to about 10, preferably from about 4 to about 7.

As with all compositions, the present compositions should not contain components which unduly interfere with the performance of the compositions.

The viscosity of the present composition is from about 1000 cps to about 7000 cps, preferably from about 200 cps to about 5000 cps.

PROCESS

First Premix

A first premix is prepared which contains all or a portion of the suspending agent(s), thickeners, viscosity modifiers, if necessary, a portion of the anionic surfactant and the water as a solvent for the solids.

First premixes for preferred compositions contain on a total composition basis from about 0.5% to about 5% EGDS, from about 0.1% to about 2% cocomonoethanolamide, from about 0.5% to about 5% anionic surfactant, from about 0.1% to about 2% ammonium xylene sulfonate, and from about 1% to about 10% water. Thus the first premix totals up to about 25% of the total composition.

The components of the premix are mixed together. The order of their addition to the premix is not critical; however, it is preferred that the surfactant and water be added first, followed by the ammonium xylene sulfonate cocomonoethanol amide, and EGDS. The premix is then heated from about 155° F. to about 170° F. (66°–71° C.).

Second Premix

A second premix is prepared containing the silicone, and, for preferred compositions, a quaternary cationic conditioning agent. This premix may also contain other thickeners such as xanthan gum, fatty alcohols, viscosity modifiers, and a portion of a surfactant material to solubilize the thicker components.

The order of raw material addition to this premix is important to proper solubilization and dispensing of the ingredients. First the solvent system including any viscosity modifier is placed into the mixer, followed by fatty alcohols if present. The quaternary cationic surfactant material is then added. The silicone is then added and dispersed. In compositions containing xanthan gum, this material is added last. The active conditioning agents are dispersed into the surfactant materials.

Second premixes for preferred compositions comprise on a total composition basis from about 1% to about 5% anionic surfactant; from about 0.5% to about 3% ammonium xylene sulfonate, from about 0.05% to about 1% tricetyimethyl ammonium chloride, from about 1% to about 5% silicone, and from 0% to about 3% xanthan gum.

When complete the premix is heated to from about 150° F. to about 170° F. (66°-71° C.).

The Main Mix

The main mix contains all other desired ingredients. The majority of the surfactant material, water, and adjuvants such as dyes, perfume, and preservatives are mixed and held at ambient temperature.

The main mix for preferred compositions comprises from about 50% to about 75% of the total composition.

Such main mix comprises on a total composition basis from about 5% to about 45% surfactant, from about 1% to about 25% water, and from about 0.01% to about 5% minor ingredients such as perfumes, dyes, and preservatives.

Injection of the Premixes

The first premix is injected into the main mix at a shear of from about 10 lb/in$^2$ to about 75 lb/in$^2$, preferably from about 15 lb/in$^2$ to about 20 lb/in$^2$. The second premix is then injected into the main mix at a pressure of from about 2 lb/in$^2$ to about 10 lb/in$^2$, preferably from about 3 lb/in$^2$ to about 6 lb/in$^2$. Where no xanthan gum is present, pressures used for the second premix may be increased to from about 5 lb/in$^2$ about 15 lb/in$^2$.

After the second premix is injected, the entire mixture is diluted with any remaining water, and cooled if necessary to an appropriate packing temperature.

The premixes may be injected via piping injection with drilled holes, mix tank vacuum injection with scrapper blades, dispersion discs, homogenizers, mills, high shear pumps or nozzles in order to provide the necessary shear. If nozzles are used, the number of nozzles is not critical and varies with the size of the batch made. The nozzles should be positioned above the agitator blades in the mixer, but close enough to inject the premixes into the area of turbulent agitation.

EXAMPLES

Preparing the Premix

| Premix | Mainmix |
|---|---|
| 7.0% ammonium laureth-3-sulfate (AES) solution (28% active) | 60.0% ammonium lauryl sulfonate (ALS) solution (25% active) |
| 0.1% cetearyl alcohol | 7.4% ammonium laureth-3-sulfate (AES) solution (28% active) |
| 3.0% polydimethyl siloxane | 0.5% xanthan gum |
| | 1.5% ethylene glycol distearate |
| | 1.5% ammonium xylene sulfonate |
| | 1.0% coconut monoethanolamide |
| | 0.5% tricetyl methyl ammonium |

| Premix | Mainmix |
|---|---|
| | chloride (TCMAC) |
| | 0.60% caustic soda, 50% NaOH |
| | 0.40% sodium chloride |
| | 0.8% cetearyl alcohol |
| | 0.65% dye |
| | 1.2% perfume |
| | 0.03% preservative |
| | qs 100.0% water |

Preparing the Premix

The AES is added to the premix tank at about 155° F. Agitation is then begun and the cetearyl alcohol is then added, followed by the polydimethyl siloxane. Do not allow tank temperature to go below 120° F. during mixing. Hold premix at from 120° F. to 160° F. until mixed with main mix.

Preparing the Main Mix

Water is added to the tank at 155° F. The agitation is begun, and sodium chloride is added. The AES and ALS are added, also at 155° F. A Triblender is engaged during ALS and xanthan gum addition. The coconut monoethanolamide is then added, followed by ethylene glycol distearate, cetearyl alcohol, tricetyl methyl ammonium chloride, caustic soda, sodium chloride, dyes, perfumes, and preservatives.

Mixing

The main mix and premix are pumped together at the appropriate ratio (9:1) through a mill and heat exchanger in order to dispense the silicone and crystallize the suspending agent. Agitation is continued for one hour.

| 1st Premix | Main Mix |
|---|---|
| 5.0% water | 5.0% water |
| 15.0% ALS (25% active) | 45.0% ammonium lauryl sulfate (ALS) (25% active) |
| 1.0% buffers | |
| 1.5% ammonium xylene sulfonate (AXS) (40% active) | 4.3% ammonium laureth sulfate (AES) (28% active) |
| | 0.71% dye |
| 1.0% coconut monoethanol amide | 0.03% preservative |
| 1.5% ethylene glycol distearate | 1.2% perfume |
| | q.s. 100% water, (dilution - added after mixing) |

| Second Premix |
|---|
| 10.0% AES (28% active) |
| 2.0% AXS (40% active) |
| 0.75% cetearyl alcohol |
| 0.6% tricetyl methyl ammonium chloride (87% active) |
| 3.0% polydimethyl siloxane |
| 0.5% xanthan gum |

Main Mix

The water, ALS, and AES are added to the tank. Color solutions, preservative, and perfume are added at ambient conditions under moderate agitation.

First Premix

Water and ALS (25% active) are added to the premix tank and heated under moderate agitation to 120° F. Buffers are then added and agitated until dissolved. Heating is continued and the AXS is added under moderate agitation. At 170° F. the preweighed CMEA is added and agitated until it melts and dissolves. At 170° F. the EGDS is added and agitated until dissolved. After five minutes of mixing the premix is pumped through a positive displacement pump and insulated pipe to a hollow cone spray nozzle which is positioned below the surface of the main mix and approximately three inches above the turbine agitator blade. Contents of tank are agitated at a high rate during injection. The premix is pumped at a rate of about 1.75 kg/min (pressure=15 lb/in$^2$) for a batch size of 200 kg. The EGDS crystallizes and a pearlescent sheen is observed on the agitated surface of the main mix tank. In order to control the main mix temperature (and optimize EGDS crystal size for appearance and stability during injection) a recirculation pump and plate and frame heat exchanger may be employed.

A small portion (1%) of the formula water is then pumped through the injection line to purge the last of the premix.

Second Premix

The AES and AXS are added to the premix tank under low agitation and heated to 120° F. The cetearyl alcohol is then added under moderate agitation and mixed until it melts and dissolves. The TCMAC is then added under moderate agitation and mixed until it melts and dissolves at 155° F. The viscous silicone gum is then allowed to flow slowly into the well agitated premix tank and allowed to mix and dissolve for 20 minutes. Finally, the xanthan gum is sprinkled slowly onto the premix surface under moderate agitation. Mix for five minutes or until all lumps have been wetted out and the mix is homogeneous. The finished second premix is then pumped through the same nozzle as the first premix, but at a lower flow rate (0.5 kg/min) and lower pressure (4 lb/in$^2$). With no external heat exchanger, the final batch temperature is 96° F. A final water rinse (1%) is then pumped through the injection lines to purge. No milling is required as the injection adequately disperses the ingredients.

The finished sample is pearlescent and smooth with a better sheen than a product made by the conventional hot process as described in the comparative single premix example. Viscosity is stable immediately after completion of process and high temperature stability is improved.

| 1st Premix | Main Mix |
|---|---|
| 5.9% water | 0.5% water |
| 15.0% ALS (25% active) | 45.0% ammonium lauryl sulfate |
| 0.4% buffers | (ALS) (25% active) |
| 1.5% ammonium xylene | 4.3% ammonium laureth sulfate |
| sulfonate (AXS) | (AES) (28% active) |
| (40% active) | 0.62% dye |
| 1.5% coconut monoethanol amide | 0.03% preservative |
| 2.0% ethylene glycol distearate | 1.2% perfume |
| 1.7% laureth-5-phosphate | 7.0% dilution water (added after mixing) |
| Second Premix | |
| 10.0% AES (28% active) | |
| 2.0% AXS (40% active) | |
| 0.75% cetearyl alcohol | |
| 0.6% tricetyl methyl ammonium chloride (TCMAC) (87% active) | |
| 3.0% polydimethyl siloxane | |

Main Mix

The water, ALS, and AES are added to the tank. Color solutions, preservative, and perfume are added at ambient conditions under moderate agitation.

First Premix

The water is added to the premix tank and heated to 150° F. A portion of the buffer and the laureth-5-phosphate are added with rapid agitation at a temperature of 170° F. and allowed to mix for about 15 minutes. After the solution becomes clear, the ALS and AXS are added and the temperature is brought up to 160° F. The remaining buffers are then added and agitated until dissolved. At 160° F. the coconut monoethanol amide is added and agitated until it melts and dissolves. Then the EGDS is added at 160° F. and agitated until it melts and dissolves. The completed premix is then held at 160° F. to 170° F. After five minutes of mixing the premix is pumped through a positive displacement pump and insulated pipe to a hollow cone spray nozzle which is positioned below the surface of the main mix and approximately three inches above the turbine agitator blade. Mixing is controlled at a high rate during injection. The premix is pumped at a rate of about 2.0 kg/min (pressure=8 lb/in$^2$) for a batch size of 175 kg. The EGDS crystallizes and a pearlescent sheen is observed on the agitated surface of the main mix tank. In order to control the main mix temperature (and optimize EGDS crystal size for appearance and stability during injection) a recirculation pump and plate and frame heat exchanger may be employed.

A small portion (1%) of the formula water is then pumped through the injection line to purge the last of the premix.

Cold water was run through the main mix jacket during and after injection.

Second Premix

The AES and AXS are added to the premix tank under low agitation and heated to 165° F. The cetearyl alchol is then added under moderate agitation and mixed until it melts and dissolves. The TCMAC is then added under moderate agitation and mixed until it melts and dissolves at 162° F. The viscous silicone gum is then allowed to flow slowly into the well agitated premix tank and allowed to mix and dissolve for 10 minutes. The finished second premix is then pumped through the same nozzle as the first premix, but at a lower flow rate (0.7 kg/min) and lower pressure (6 lb/in$^2$). With no external heat exchanger, the final batch temperature is 95° F. A final water rinse (1%) is then pumped through the injection lines to purge, and dilution water is added to the batch to bring to 100%.

The finished sample is pearlescent and smooth with a better sheen than a product made by the conventional hot process.

What is claimed is:

1. A process for making a slicone-containing shampoo composition comprising the steps of:
   (a) preparing a first premix comprising:
      (i) from about 0.5% to about 5% ethylene glycol distearate;
      (ii) from about 1% to about 10% of an anionic surfactant;
      (iii) from about 0.1% to about 5% of a viscosity modifier;

(iv) from about 0.1% to about 5% cocomonoethanol amide; and
(v) from about 1% to about 10% water;

(b) preparing a second premix comprising:
  (i) from about 0.01% to about 10% of a silicone conditioning agent;
  (ii) from about 0.1% to about 5% ammonium xylene sulfonate;
  (iii) from about 0.01% to about 5% cetearyl alcohol;
  (iv) from about 0.01% to about 5% tricetyl methyl ammonium chloride;
  (v) from about 1% to about 10% of an anionic surfactant; and
  (vi) from 0.3% to about 3% xanthan gum.

(c) preparing a main mix comprising all other desired ingredients, including adjuvants;
(d) heating the premixes separately to a temperature of from about 150° F. to about 170° F.;
(e) injecting the premixes sequentially into the main mix, which is at ambient temperature; and
(f) allowing the composition to cool.

2. A process according to claim 1 wherein the main mix comprises on a total composition basis:
(a) from about 5% to about 40% of an anionic surfactant;
(b) from 0% up to about 5% perfume;
(c) from 0% up to about 5% dye; and
(d) from 20% to about 30% water.

3. A shampoo composition made by the process of claim 1.

4. A shampoo composition made by the process of claim 1 comprising:
(a) from about 5% to about 60% of an anionic surfactant selected from the group consisting of ammonium lauryl sulfate, ammonium laureth sulfate, and mixtures thereof;
(b) from about 01% to about 10% polydimethyl siloxane;
(c) from about 0.5% to about 5% ethylene glycol distearate;
(d) from about 0.1% to about 1% coconut monoethanolamide;
(e) from about 1% to about 5% of a hydrotrope;
(f) from about 0.01% to about 5% tricetyl methyl ammonium chloride; and
(g) from 0.1% to about 5% of an alkyl ethoxylated phosphoric acid monoester.

5. A shampoo composition according to claim 4 wherein the alkyl ethoxylated phosphoric acid monoester is selected from the group consisting of laureth-3-phosphate, oleth-3-phosphate, laureth-4-phosphate, and laureth-5-phosphate.

* * * * *